United States Patent [19]

Caton et al.

[11] 4,158,062
[45] Jun. 12, 1979

[54] CYCLOPENTANE DERIVATIVES

[75] Inventors: Michael P. L. Caton; Edward C. J. Coffee, both of Upminster, England; Gordon L. Watkins, Burbank, Calif.

[73] Assignee: May & Baker Limited, Essex, England

[21] Appl. No.: 909,018

[22] Filed: May 24, 1978

[30] Foreign Application Priority Data

May 26, 1977 [GB] United Kingdom ............... 22319/77

[51] Int. Cl.$^2$ ...................... A61K 31/12; C07C 49/28
[52] U.S. Cl. ................................. 424/331; 260/590 C
[58] Field of Search ...................... 424/331; 260/590 C

[56] References Cited
U.S. PATENT DOCUMENTS 4,088,695  5/1978  Caton et al. ..................... 260/590 C Primary Examiner—Frederick E. Waddell Attorney, Agent, or Firm—Stevens, Davis, Miller & Mosher

[57] ABSTRACT

Compounds of the formula:

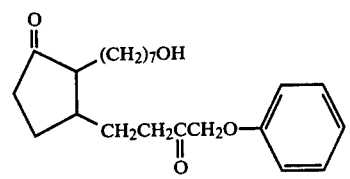

wherein the two side chains are attached to the ring carbon atoms in the trans configuration, have pharmacological properties typical of prostaglandins, and are especially useful for the treatment of gastric ulceration and gastric hyperacidity.

6 Claims, No Drawings

CYCLOPENTANE DERIVATIVES

This invention relates to new cyclopentane derivatives possessing pharmacological properties, to a process for their preparation, and to pharmaceutical compositions containing them.

In the specification of British Pat. No. 1468830, as well as in the specifications of the corresponding overseas applications, for example Dutch patent application No. 75,00868 and U.S. Pat. No. 4,088,695, there are described new cyclopentane derivatives of the general formula:

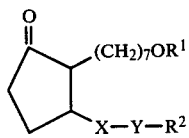

wherein $R^1$ represents a hydrogen atom or a carboxylic acyl group, and either (i) $R^2$ represents a group of the general formula:

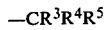
$$-CR^3R^4R^5 \qquad II$$

(wherein $R^3$ and $R^4$ are identical or different and each represents a hydrogen atom or a straight- or branched-chain alkyl group containing from 1 to 4 carbon atoms, $R^5$ represents a hydrogen atom or a straight- or branched-chain alkyl group containing from 1 to 10 carbon atoms, a straight- or branched-chain alkoxy group containing from 1 to 10 carbon atoms, a cycloalkyl group containing from 5 to 7 carbon atoms, an adamantyl group, or represents a straight- or branched-chain alkyl group containing from 1 to 6 carbon atoms substituted by a straight- or branched-chain alkoxy group containing from 1 to 6 carbon atoms, by a cycloalkyl group containing from 5 to 7 carbon atoms or by an adamantyl group, or the group $-CR^3R^4R^5$ together forms a cycloalkyl group containing from 5 to 7 carbon atoms, or an adamantyl group), X represents a trans-vinylene or an ethylene group, and Y represents a carbonyl group or a group of the general formula:

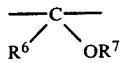

wherein $R^6$ represents a hydrogen atom or a straight- or branched-chain alkyl group containing from 1 to 4 carbon atoms and $R_7$ represents a hydrogen atom or a carboxylic acyl group, or else (ii) $R^2$ represents a group of the general formula:

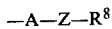
$$-A-Z-R^8 \qquad IV$$

[wherein A represents a straight- or branched-alkylene chain containing from 1 to 12 carbon atoms, Z represents a direct bond or an oxygen or sulphur atom, and $R^8$ represents an aryl or heterocyclyl group which may be substituted, for example by one or more substituents selected from halogen atoms, straight- or branched-chain alkyl and alkoxy groups containing from 1 to 6 carbon atoms, and trihalomethyl, e.g. trifluoromethyl groups], X in formula I represents an ethylene or trans-vinylene group and Y in formula I represents a carbonyl group or a group of formula III (wherein $R^6$ and $R^7$ are as hereinbefore defined), or else (iii) $R^2$ represents a group $R^8$ as hereinbefore defined, and X and Y in formula I represent simultaneously ethylene and carbonyl, trans-vinylene and carbonyl, or ethylene and $-CH(OR^7)$- groups respectively ($R^7$ being as hereinbefore defined).

In the aforementioned specifications it is pointed out that the structure shown in general formula I has at least two centres of chirality, these two centres of chirality being at the ring carbon atoms to which the side chains $-(CH_2)_7OR^1$ and $-X-Y-R^2$ are attached. In addition to these two centres of chirality, a further centre of chirality will occur when Y represents a group of formula III, and still further centres of chirality may occur in the groups $R^1$ and $R^2$. The presence of centres of chirality, as is well known, leads to the existence of isomerism. However, it is stated in the aforementioned specifications that the compounds of formula I all have such a configuration that the said side chains $-(CH_2)_7OR^1$ and $-X-Y-R^2$ attached to the said ring carbon atoms are trans with respect to each other, and that all isomers of general formula I, and mixtures thereof, which have the said side chains $-(CH_2)_7OR^1$ and $-X-Y-R^2$ attached to the ring carbon atoms in the trans configuration are within the scope of the invention described in the said specifications.

In the aforesaid specifications it is mentioned that the compounds of formula I possess valuable pharmacological properties, for example, properties typical of the related series of natural products known as prostaglandins, including, for example, the inhibition of gastric acid secretion, the production of hypotension, bronchodilatation, the stimulation of uterine contraction, the production of hypocholesteraemia and hypolipidaemia, and the stimulation of luteolysis.

As a result of further extensive research and experimentation, it has now been found that the compounds of formula I wherein $R^1$ represents a hydrogen atom, $R^2$ represents a group of formula IV [wherein A represents a methylene group (i.e. an alkylene chain containing only one carbon atom), Z represents an oxygen atom, and $R^8$ represents a phenyl group], X represents an ethylene group and Y represents a carbonyl group, possess outstanding utility, more especially in the treatment or prevention of gastric ulceration and gastric hyperacidity with unusually low activity in causing undesired side-effects, for example diarrhoea.

Thus, the present invention provides compounds of the formula:

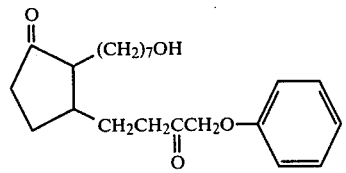

wherein the two side chains are attached to the ring carbon atoms in the trans configuration, that is to say 2-hydroxymethyl-16-phenoxy-15-oxo-13,14-dihydro-2-decarboxy-11,15-dideoxy-17,18,19,20-tetranorprostaglandin $E_1$ and its enantiomer and mixtures thereof.

A particularly important mixture of the compounds of formula V is that in which the two enantiomeric forms are present in equal proportions, i.e. $(\pm)$-2-hydroxymethyl-16-phenoxy-15-oxo-13,14-dihydro-2- decarboxy-11,15-dideoxy-17,18,19,20-tetranorprostaglandin $E_1$.

Although the compounds of formula V and mixtures thereof fall within the scope of general formula I, they have not been specifically described or characterised hitherto.

In laboratory tests, the activities of (±)-2-hydroxymethyl-16-phenoxy-15-oxo-13,14-dihydro-2-decarboxy-11,15-dideoxy-17,18,19,20-tetranorprostaglandin $E_1$ in:

(i) reducing gastric acid secretion in rats;

(ii) antagonising gastric ulceration induced in rats by treatment with indomethacin; and (iii) overcoming the constipation induced in rats by treatment with morphine (an indication of the potential of the compound to produce the undesired side-effect of diarrhoea); have been determined.

The $ED_{50}$ figures given hereafter are defined as the calculated mean oral doses required to reduce gastric acid secretion, to antagonise gastric ulceration, and to overcome constipation, respectively, to 50% of the control values.

The $ED_{50}$ results were:

(i) 0.010–0.015 mg/kg animal body weight;

(II) 0.02 mg/kg animal body weight; and (iii) 3.5 mg/kg animal body weight.

These results demonstrate that the dose required to reduce gastic acid secretion and antagonise gastric ulceration is far lower than the dose required to overcome constipation. Therefore the compound may be administered to the patient at a dose which will alleviate gastric ulceration and gastric hyperacidity with little or no concomitant diarrhoea, especially when administered by the oral route.

When the compounds of formula V are compared with the related compounds described in our aforementioned specifications, it is found that the compounds of formula V possess important and unexpected advantages over the known compounds in the treatment of gastric ulceration and gastric hyperacidity with little or no concomitant diarrhoea and without unwanted contraction of the uterus.

In laboratory tests similar to those mentioned above, such advantages were demonstrated over the folllowing four comparison compounds described in our aforementioned specifications:

T. 7-[2-(3-hydroxy-4-phenoxybut-trans-1enyl)-5-oxocyclopetyl]heptanol;

U. 7-[2-(4-methyl-3-oxooct-trans-1-enyl)-5-oxocyclopentyl]heptanol;

V. 7-[5-(3-oxo-5-phenylpent-trans-1-enyl)-2-oxocyclopentyl]heptanol; and

W. 7-[5-(3-oxo-4-phenylbut-trans-1-enyl)-2-oxocyclopentyl]heptanol.

The reference letters T, U, V and W are allocated for the purpose of convenience in the present specification. Similarly, the (±) mixture of enantiomers of formula V is allocated the reference letter A.

In the laboratory tests:

1. Compound U produced little reduction of gastric acid secretion in the rat when administered at an oral dose 20 times greater than the effective does of compound A.

2. Compounds V and W failed to prevent the occurrence of indomethacin-induced gastric ulceration in the rat when administered at oral doses 50 times greater than the effective dose of compound A.

3. Although the compound T showed similar levels of oral activity to those of compound A in reducing gastric acid activity in rats and in antagonising indomethacin-induced gastric ulceration in rats, compound T was 10 times as active as compound A in the stimulation of uterine contraction. It will be understood that unplanned stimulation of uterine contraction in patients being treated for gastric hyperacidity or gastric ulceration would be unwanted in all cases.

The compounds of formula V and mixtures thereof may be prepared by the application or adaptation of the methods described in our aforementioned specifications for the preparation of compounds of general formula I.

Thus, the compounds of general formula V may be prepared by the reduction of the carbon-carbon double bond in the corresponding compounds of the formula:

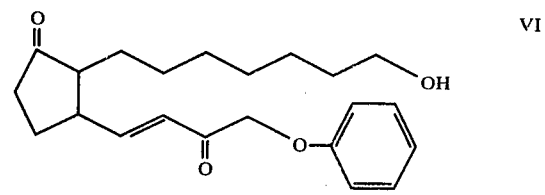

in conditions which do not appreciably affect carbonyl groups, for example by hydrogenation in the presence of a catalyst, for example rhodium on charcoal or palladium on charcoal, in the presence of an inert organic solvent, for example an alkanol containing from 1 to 3 carbon atoms, e.g. ethanol. The hydrogenation can conveniently be carried out at the ambient temperature and at an elevated pressure, e.g. at a hydrogen pressure of between 0.5 and 10 kg/cm$^2$.

The compounds of formula VI may be prepared by the hydrolysis of corresponding compounds of the formula:

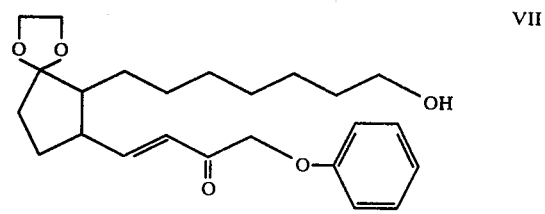

The hydrolysis is generally carried out in acidic conditions, for example by reaction with a dilute inorganic acid, e.g. dilute hydrochloric acid, preferably at above room temperature, e.g. between 50° and 70° C., or by means of an organic acid in the presence of water, for example aqueous acetic acid, e.g. 40–80% v/v aqueous acetic acid, or p-toluenesulphonic acid in acetone containing a small amount of water, preferably at temperatures between 5° and 100° C., more particularly between 15° and 30° C. Alternatively, the compounds of formula VII may be converted to the compounds of formula VI by subjecting them to chromatography, preferably using an eluant containing an organic acid, for example glacial acetic acid or formic acid. By this means purification is effected simultaneously with hydrolysis.

The preparation of compounds of formula VII is described in detail in our aforementioned specifications.

As will be readily appreciated by those skilled in the art, the enantiomeric forms of the compounds of the invention arising from the aforementioned centres of chirality may be separated by the application or adaptation of known methods.

By the term "known methods" as used in this specification is meant methods heretofore used or described in the literature.

The following Example illustrates the present invention.

EXAMPLE 1

(i)
(±)-2-Hydroxymethyl-16-phenoxy-15-oxo-13,14-dihydro-2-decarboxy-11,15-dideoxy-17,18,19,20-tetranorprostaglandin $E_1$ A solution of (±)-2-hydroxymethyl-16-phenoxy-15-oxo-2-decarboxy-11,15-dideoxy-17,18,19,20-tetranorprostaglandin $E_1$ (350 mg) in ethanol (25 ml) was hydrogenated in the presence of a palladium on charcoal catalyst (5% w/w) at room temperature and 4.9 kg/cm² hydrogen pressure. The mixture was then filtered through diatomaceous earth and the filtrate was evaporated in vacuo. The resulting residue was purified by preparative thin layer chromatography on silica adsorbent, using as eluant a mixture of ethyl acetate, cyclohexane and 90% w/w aqueous formic acid (40:40:1 by volume), to give (±)-2-hydroxymethyl-16-phenoxy-15-oxo-13,14-dihydro-2-decarboxy-11,15-dideoxy-17,18,19,20-tetranorprostaglandin $E_1$ (85 mg). [Elemental analysis: C, 72.8; H, 9.0%; $C_{22}H_{32}O_4$ requires C, 73.3; H, 8.9%. Infra-red spectrum $\nu$3450, 1740, 750, 690 cm$^{-1}$. Nuclear magnetic resonance spectrum (deuterochloroform): multiplet at 1.1–2.9$\delta$, triplet at 3.6$\delta$, singlet at 4.6$\delta$, multiplet at 6.8–7.5$\delta$].

Refer to (ii) and (iii) hereafter for the preparation of the starting material of (i) above.

(ii)
(±)-2-Hydroxymehtyl-16-phenoxy-15-oxo-2-decarboxy-11,15-dideoxy-17,18,19,20-tetranorprostaglandin $E_1$ A mixture of 6-(7-hydroxyheptyl)-7-(3-oxo-4-phenoxybut-trans-1-enyl)-1,4-dioxaspiro[4,4]nonane (400 mg), aqueous acetic acid (20 ml; 50% v/v) and tetrahydrofuran (10ml) was stirred at 40° C. for four hours. The solvents were then evaporated off in vacuo and the residue was purified by preparative thin layer chromatography on silica adsorbent, using an eluant a mixture of ethyl acetate, cyclohexane and 90% w/w aqueous formic acid (40:40:1 by volume), to give (±)-2-hydroxymethyl-16-phenoxy-15-oxo-2-decarboxy-11,15-dideoxy-17,18,19,20-tetranorprostaglandin $E_1$ (67 mg) [Elemental analysis: C, 73.7; H, 8.8%; $C_{22}H_{30}O_4$ requires: C, 73.7; H, 8.4%. Infra-red spectrum $\nu$3450, 1740, 1690, 750, 690 cm$^{-1}$].

(iii)
6-(7-Hydroxyheptyl)-7-(3-oxo-4-phenoxybut-trans-1-enyl)-1,4-dioxaspiro[4,4]nonane A solution of dimethyl 2-oxo-3-phenoxypropyl-phosphonate (43 g) in dry tetrahydrofuran (150 ml) was added dropwise to a stirred suspension of sodium hydride (3.6) in tetrahydrofuran (200 ml; dried over sodium) under nitrogen at room temperature. The temperature rose to 45° C. and the mixture was stirred for 30 minutes, and then a solution of 7-formyl-6-(7-hydroxyheptyl)-1,4-dioxaspiro[4,4]nonane (18.9 g; prepared as described in the specification of U.S. Pat. No. 3,880,883) in dry tetrahydrofuran (100 ml) was added slowly to the mixture at 43° C. The mixture was stirred at 43° to 47° C. for 3 hours, and was then cooled, filtered and evaporated in vacuo. The residue was dissolved in diethyl ether (100 ml) and the ethereal solution was washed with water (3×100 ml.). After drying over magnesium sulphate, the ethereal solution was evaporated to give a brown oil (24.28 g), which was purified further by chromatography on a silicic acid column (250 g Merck Kieselgel 60), eluting with diethyl ether, to give 6-(7-hydroxyheptyl)-7-(3-oxo-4-phenoxybut-trans-1enyl)-1,4-dioxaspiro[4,4]-nonane (7.88 g). [Elemental analysis: C, 71.8; H, 8.7%; $C_{24}H_{34}O_5$ requires: C, 71.6; H, 8.5%. Infra-red spectrum: $\nu$3450, 1690, 950, 750, 690 cm$^{-1}$. Nuclear magnetic resonance spectrum (deuterochloroform): 0.8 to 2.7$\delta$ (multiplet), 3.5 to 3.8$\delta$ (triplet), 3.95$\delta$, 4.75$\delta$ (singlet), 6.3 to 7.5$\delta$ (multiplet)].

The present invention includes within its scope pharmaceutical compositions which comprise a compound of formula V together with a pharmaceutical carrier or coating. In clinical practice the compounds of the present invention will normally be administered orally, rectally, vaginally or parenterally.

Solid compositions for oral administration include compressed tablets, pills, dispersible powders, and granules.

Liquid compositions for oral administration include pharmaceutically-acceptable emulsions, solutions, suspensions, syrups and elixirs.

The compositions according to the invention, for oral administration, also include capsules of absorbable material such as gelatin containing one or more of the compounds of the invention.

Solid compositions for vaginal administration include pessaries.

Solid compositions for rectal administration include suppositories.

Preparations according to the invention for parenteral administration include sterile aqueous or non-aqueous solutions, suspensions, or emulsions.

The compounds of the invention may alternatively be administered orally by any method known per se for administration by inhalation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. The active ingredients may also be administered orally by inhalation in the form of aerosols generated from self-propelling pharmaceutical compositions.

Methods of presentation of pharmaceutically active compounds are well known in the art and a suitable vehicle may be determined by the physician, pharmacist or veterinarian, depending upon such factors as the effect sought, the size, age, sex and condition of the patient and, for veterinary uses, species of the animal to be treated, and on the physical properties of the active compound. The compositions may also contain, as is usual in the art, such materials as solid or liquid diluents, wetting agents, preservatives, flavouring and colouring agents and the like.

The percentage of active ingredient in the compositions of the invention may be varied, it being necessary that it should constitute a proportion such that a suitable dosage for the therapeutic effect desired shall be obtained. Obviously several unit dosage forms may be administered at about the same time.

In general, the compositions should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment. In the adult, the doses are generally, for example, between 0.02 and 2.0 mg by aerosol administration, between 0.0002 and 2.0 mg/kg body weight by intravenous administration, and between 0.001 and 1.0 mg/kg body weight orally. If necessary these doses may be repeated as and when required.

As stated hereinbefore the compounds of formula V are of particular utility in the treatment of patients with gastric ulceration and of patients with gastric hyperacidity, especially when administered by the oral route.

The compounds reduce the extent of gastric ulceration or prevent the increase of gastric ulceration. Furthermore, they reduce the level of gastric acid secretion, especially excessive gastric acid secretion stimulated by food or stress, and thus they reduce exacerbation of the symptoms of the ulceration caused by the gastric acid.

At oral doses of above 1.0 mg the compounds of formula V may cause vomiting and diarrhoea but for these compounds such a dose level is in excess of that which is generally required in the treatment of gastric ulceration and gastric hyperacidity. Accordingly, the appearance of undesirable side-effects may be avoided by the selection of suitable dose rates.

For example, compounds of formula V may be administered orally at doses of 0.01 mg/kg body weight in liquid compositions, or at doses of 0.02 mg/kg body weight in capsules, without the appearance of vomiting and diarrhoea and unwanted contraction of the uterus.

Thus, for the treatment of adult patients with gastric ulceration and of adult patients with gastric hyperacidity, oral doses of between 0.001 and 0.05 mg of a compound of formula V per kg body weight are generally suitable, particularly oral doses of between 0.001 and 0.01 mg. of a compound of formula V per kg body weight in the form of a liquid composition or of between 0.001 and 0.02 mg of a compound of formula V per kg body weight in the form of capsules, administered 2, 3 or 4 times per day.

The following Examples illustrate pharmaceutical compositions according to the invention.

EXAMPLE 2

Gelatin capsules (No. 2 size) were made up in the conventional manner, with the following contents:

| | |
|---|---|
| (±)-2-hydroxymethyl-16-phenoxy-15-oxo-13,14-dihydro-2-decarboxy-11,15-dideoxy-17,18,19,20-tetranorprostaglandin E$_1$ | 0.3 mg |
| lactose | 175 mg |
| starch | 25 mg |
| magnesium stearate | 2 mg |
| Aerosil (finely divided silicon dioxide) | 2 mg. |

EXAMPLE 3

Gelatin capsules (No. 2 size) were made up in the conventional manner, with the following contents:

| | |
|---|---|
| (±)-2-hydroxymethyl-16-phenoxy-15-oxo-13,14-dihydro-2-decarboxy-11,15-dideoxy-17,18,19,20-tetranorprostaglandin E$_1$ | 0.3 mg |
| propylene glycol | 0.2 ml. |

We claim:

1. A compound of the formula:

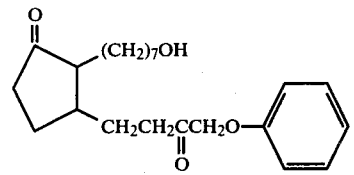

wherein the two side chains are attached to the ring carbon atoms in the trans configuration.

2. A compound according to claim 1 which is (±)-2-hydroxymethyl-16-phenoxy-15-oxo-13,14-dihydro-2-decarboxy-11,15-dideoxy-17,18,19,20-tetranorprostaglandin E$_1$.

3. A pharmaceutical composition useful in the treatment or prevention of gastric ulceration and gastric hyperacidity which comprises, as active ingredient, an effective amount of a compound of the formula depicted in claim 1 together with a pharmaceutical carrier.

4. A method for the treatment or prevention of gastric ulceration and gastric hyperacidity in a patient which comprises administering to the patient an effective amount of a compound of the formula depicted in claim 1.

5. A method according to claim 4 for the treatment of adult patients with gastric ulceration and of adult patients with gastric hyperacidity in which oral doses of between 0.001 and 0.05 mg/kg body weight of a compound of the formula depicted in claim 1 in the form of a liquid pharmaceutically-acceptable composition, or of between 0.001 and 0.02 mg/kg body weight of a compound of the formula depicted in claim 1 in the form of capsules of absorbable material, is administered two, three of four times per day to the patient.

6. A method according to claim 4 or 5 in which the amount of the compound of the formula depicted in claim 1 administered orally to the patient is 0.01 mg/kg body weight in liquid pharmaceutically-acceptable compositions or 0.02 mg/kg body weight in capsules of absorbable material.

* * * * *